(12) United States Patent
Thomas et al.

(10) Patent No.: US 11,471,165 B2
(45) Date of Patent: Oct. 18, 2022

(54) LIGATION CLIP CARTRIDGE

(71) Applicant: Covidien LP, Mansfield, MA (US)

(72) Inventors: Justin Thomas, New Haven, CT (US); Roy J. Pilletere, North Haven, CT (US); Matthew A. Dinino, Newington, CT (US); Gregory R. Morck, Haddam, CT (US); Eric Brown, Madison, CT (US); Jacob C. Baril, Norwalk, CT (US)

(73) Assignee: Covidien LP, Mansfield, MA (US)

( * ) Notice: Subject to any disclaimer, the term of this patent is extended or adjusted under 35 U.S.C. 154(b) by 232 days.

(21) Appl. No.: 16/830,417

(22) Filed: Mar. 26, 2020

(65) Prior Publication Data

US 2020/0352575 A1    Nov. 12, 2020

Related U.S. Application Data

(60) Provisional application No. 62/844,911, filed on May 8, 2019.

(51) Int. Cl.
*A61B 17/122*   (2006.01)
*A61B 17/00*    (2006.01)
*A61B 50/30*    (2016.01)

(52) U.S. Cl.
CPC ........ *A61B 17/1222* (2013.01); *A61B 17/122* (2013.01); *A61B 2017/00862* (2013.01); *A61B 2017/00902* (2013.01); *A61B 2017/00955* (2013.01); *A61B 2050/3015* (2016.02)

(58) Field of Classification Search
CPC .............. A61B 17/1222; A61B 17/122; A61B 2050/3015; A61B 17/10; A61B 17/08
See application file for complete search history.

(56) References Cited

U.S. PATENT DOCUMENTS

| | | |
|---|---|---|
| 3,439,523 A | 4/1969 | Wood |
| 3,713,533 A | 1/1973 | Reimels |
| 4,076,120 A | 2/1978 | Carroll et al. |
| 4,146,130 A | 3/1979 | Samuels et al. |
| 4,187,712 A | 2/1980 | Samuels et al. |
| 4,212,303 A | 7/1980 | Nolan |
| 4,212,390 A | 7/1980 | Raczkowski et al. |
| 4,294,355 A | 10/1981 | Jewusiak et al. |
| 4,344,531 A | 8/1982 | Giersch |

(Continued)

FOREIGN PATENT DOCUMENTS

| | | |
|---|---|---|
| BE | 654195 A | 2/1965 |
| CN | 204839635 U | 12/2015 |

(Continued)

OTHER PUBLICATIONS

European Search Report dated Sep. 24, 2020, for corresponding EP Appln. No. 20173032, 11 pages.

(Continued)

*Primary Examiner* — Katherine H Schwiker
*Assistant Examiner* — Serenity A Miller (57) ABSTRACT

A ligation clip cartridge includes a housing and one or more retaining members. The housing defines a plurality of clip recesses that receive ligation clips. The retaining members are positioned on the housing to engage the clips within the housing in an unbiased state to minimize damage to the clip material caused by strain on the clip.

16 Claims, 8 Drawing Sheets

(56) References Cited

U.S. PATENT DOCUMENTS

| | | | |
|---|---|---|---|
| 4,346,869 A | 8/1982 | MacNeill | |
| 4,361,229 A | 11/1982 | Mericle | |
| 4,390,019 A | 6/1983 | LeVeen et al. | |
| 4,412,617 A | 11/1983 | Cerwin | |
| 4,418,694 A | 12/1983 | Beroff et al. | |
| 4,449,531 A | 5/1984 | Cerwin et al. | |
| 4,485,953 A | 12/1984 | Rothfuss | |
| 4,487,205 A | 12/1984 | Di Giovanni et al. | |
| 4,550,729 A | 11/1985 | Cerwin et al. | |
| 4,696,396 A | 9/1987 | Samuels | |
| 4,726,372 A | 2/1988 | Perlin | |
| 4,834,096 A | 5/1989 | Oh et al. | |
| 4,936,447 A | 6/1990 | Peiffer | |
| 4,942,886 A | 7/1990 | Timmons | |
| 4,961,499 A | 10/1990 | Kulp | |
| 4,971,198 A | 11/1990 | Mericle | |
| 4,972,949 A | 11/1990 | Peiffer | |
| 5,046,611 A | 9/1991 | Oh | |
| 5,046,624 A | 9/1991 | Murphy et al. | |
| 5,050,272 A | 9/1991 | Robinson et al. | |
| 5,062,846 A | 11/1991 | Oh et al. | |
| 5,100,416 A | 3/1992 | Oh et al. | |
| 5,201,416 A | 4/1993 | Taylor | |
| 5,279,416 A | 1/1994 | Malec et al. | |
| 5,423,831 A | 6/1995 | Nates | |
| 5,564,262 A | 10/1996 | Bevis et al. | |
| 5,634,930 A | 6/1997 | Thornton et al. | |
| 5,676,676 A | 10/1997 | Porter | |
| 5,697,942 A | 12/1997 | Palti | |
| 5,713,912 A | 2/1998 | Porter | |
| 5,846,255 A | 12/1998 | Casey | |
| 5,908,430 A | 6/1999 | Appleby | |
| 5,921,991 A | 7/1999 | Whitehead et al. | |
| 6,044,971 A | 4/2000 | Esposito et al. | |
| 6,158,583 A | 12/2000 | Forster | |
| 6,217,590 B1 | 4/2001 | Levinson | |
| 6,228,097 B1 | 5/2001 | Levinson et al. | |
| 6,273,253 B1 | 8/2001 | Forster et al. | |
| 6,306,150 B1 | 10/2001 | Levinson | |
| 6,349,727 B1 | 2/2002 | Stewart, Jr. | |
| 6,391,035 B1 | 5/2002 | Appleby et al. | |
| 6,419,682 B1 | 7/2002 | Appleby et al. | |
| 6,421,920 B1 | 7/2002 | Jensen | |
| 6,439,727 B1 | 8/2002 | Koide | |
| 6,460,700 B2 | 10/2002 | Weisshaupt | |
| 6,460,749 B1 | 10/2002 | Levinson et al. | |
| 6,780,195 B2 | 8/2004 | Porat | |
| 6,824,547 B2 | 11/2004 | Wilson, Jr. et al. | |
| 6,863,675 B2 | 3/2005 | Wilson, Jr. | |
| 6,880,699 B2 | 4/2005 | Gallagher | |
| 7,001,412 B2 | 2/2006 | Gallagher et al. | |
| 7,052,504 B2 | 5/2006 | Hughett | |
| 7,131,977 B2 | 11/2006 | Fowler | |
| 7,144,402 B2 | 12/2006 | Kuester, III | |
| 7,211,091 B2 | 5/2007 | Fowler et al. | |
| 7,211,092 B2 | 5/2007 | Hughett | |
| 7,316,696 B2 | 1/2008 | Wilson, Jr. et al. | |
| 7,326,223 B2 | 2/2008 | Wilson, Jr. | |
| 7,452,368 B2 | 11/2008 | Liberatore et al. | |
| 7,585,304 B2 | 9/2009 | Hughett | |
| 7,628,272 B2 | 12/2009 | Wiedenbein | |
| 7,857,129 B2 | 12/2010 | Iaconi-Forrer et al. | |
| 8,042,687 B2 | 10/2011 | Cannady | |
| 8,312,992 B2 | 11/2012 | Disch | |
| 8,403,138 B2 | 3/2013 | Weisshaupt et al. | |
| 8,425,515 B2 | 4/2013 | Gamache et al. | |
| 8,627,955 B2 | 1/2014 | Weisshaupt et al. | |
| 8,839,954 B2 | 9/2014 | Disch | |
| 8,888,398 B2 | 11/2014 | Werth | |
| 9,271,737 B2 | 3/2016 | Castro et al. | |
| 9,282,972 B1 | 3/2016 | Patel et al. | |
| 9,445,820 B2 | 9/2016 | Whiting | |
| 9,456,824 B2 | 10/2016 | Willett et al. | |
| 9,480,480 B2 | 11/2016 | Santilli et al. | |
| 9,486,225 B2 | 11/2016 | Michler et al. | |
| 9,517,178 B2 | 12/2016 | Chancibot | |
| D808,522 S | 1/2018 | Cannady et al. | |
| 9,855,053 B2 | 1/2018 | Bagaoisan et al. | |
| 10,130,373 B2 | 11/2018 | Castro et al. | |
| 10,136,898 B2 | 11/2018 | Schmidt et al. | |
| 2002/0046961 A1 | 4/2002 | Levinson et al. | |
| 2002/0177863 A1 | 11/2002 | Mandel et al. | |
| 2004/0040875 A1 | 3/2004 | Gallagher | |
| 2004/0199178 A1 | 10/2004 | Small | |
| 2005/0165423 A1 | 7/2005 | Gallagher et al. | |
| 2005/0165424 A1 | 7/2005 | Gallagher et al. | |
| 2006/0089659 A1 | 4/2006 | Small | |
| 2006/0124485 A1 | 6/2006 | Kennedy | |
| 2006/0217749 A1 | 9/2006 | Wilson et al. | |
| 2007/0083218 A1 | 4/2007 | Morris | |
| 2007/0118161 A1 | 5/2007 | Kennedy et al. | |
| 2007/0149988 A1 | 6/2007 | Michler et al. | |
| 2007/0149989 A1 | 6/2007 | Santilli et al. | |
| 2009/0088783 A1 | 4/2009 | Kennedy et al. | |
| 2009/0152147 A1* | 6/2009 | Cannady | A61B 17/1222 206/339 |
| 2009/0171380 A1 | 7/2009 | Whiting | |
| 2011/0224700 A1 | 9/2011 | Schmidt et al. | |
| 2011/0295291 A1 | 12/2011 | Trivisani | |
| 2012/0083803 A1 | 4/2012 | Patel et al. | |
| 2012/0226291 A1 | 9/2012 | Malizia et al. | |
| 2013/0245651 A1 | 9/2013 | Schmidt et al. | |
| 2013/0253540 A1 | 9/2013 | Castro et al. | |
| 2013/0261642 A1 | 10/2013 | Willett et al. | |
| 2014/0054192 A1 | 2/2014 | Chancibot | |
| 2014/0243862 A1 | 8/2014 | Bagaoisan et al. | |
| 2014/0276970 A1 | 9/2014 | Messerly et al. | |
| 2016/0151073 A1 | 6/2016 | Castro et al. | |
| 2016/0354089 A1 | 12/2016 | Whiting | |
| 2017/0020530 A1 | 1/2017 | Willett et al. | |
| 2017/0027576 A1 | 2/2017 | Castro | |
| 2017/0209151 A1 | 7/2017 | Brown | |
| 2017/0238935 A1 | 8/2017 | Shi | |
| 2017/0252042 A1 | 9/2017 | Kethman et al. | |
| 2018/0036008 A1 | 2/2018 | Ramsey et al. | |
| 2018/0168659 A1 | 6/2018 | Bagaoisan et al. | |
| 2018/0185029 A1 | 7/2018 | Lebens, III | |
| 2018/0228492 A1 | 8/2018 | Aranyi et al. | |
| 2018/0271527 A1 | 9/2018 | Shellenberger | |
| 2018/0271532 A1 | 9/2018 | Shellenberger | |
| 2018/0271535 A1 | 9/2018 | Shellenberger et al. | |
| 2018/0271536 A1 | 9/2018 | Shellenberger et al. | |
| 2019/0008521 A1 | 1/2019 | Brodaczewski et al. | |
| 2019/0133590 A1 | 5/2019 | Richard | |
| 2019/0159782 A1 | 5/2019 | Kamaraj et al. | |
| 2019/0223874 A1 | 7/2019 | Pilletere et al. | |

FOREIGN PATENT DOCUMENTS

| | | |
|---|---|---|
| CN | 106264647 A | 1/2017 |
| DE | 10116168 A1 | 11/2001 |
| GB | 2353710 A | 3/2001 |

OTHER PUBLICATIONS

Chinese International PCT Application No. PCT/CN2018/078294 filed Mar. 7, 2018, Covidien LP.

* cited by examiner

LIGATION CLIP CARTRIDGE

CROSS-REFERENCE TO RELATED APPLICATION

This application claims the benefit of and priority to U.S. Provisional Patent Application No. 62/844,911 filed Mar. 8, 2019, the entire disclosure of which is incorporated by reference herein.

FIELD

This disclosure is directed to a clip cartridge and, more particularly, to a clip cartridge for polymeric ligation clips.

BACKGROUND

Clip cartridges for supporting polymeric clips are known and typically include a base portion and a retaining member or retaining members. The base portion defines a number of slots that include supporting elements for supporting individual clips within the slots. The retaining member(s) is secured to the base portion and is configured engage a clip or clips to retain the clip or clips within the respective slots of the base portion on the supporting elements. A clip applier is inserted into the slots to remove a clip from the slot and to load a clip onto the clip applier.

In known clip cartridges, the retaining member(s) applies a load on the clip or clips to retain the clip or clips within the respective slots of the clip cartridge in a compressed or pre-loaded state. The retaining member may also obstruct visualization of the clip within the slot of the staple cartridge which may make loading of a clip into a clip applier difficult.

SUMMARY

One aspect of the disclosure is directed to a clip cartridge including a housing, at least one retainer, and a plurality of clips. The housing includes a body having side walls defining a central cavity and a plurality of dividing walls extending across the central cavity. Each of the plurality of dividing walls defines a transverse axis and forms a clip recess within the central cavity with an adjacent one of the plurality of dividing walls. A support member is positioned within each of the clip recesses and includes a first support surface and a second support surface. The plurality of clips is supported within the central cavity of the housing, with one clip being supported within each of the clip recesses. Each clip has first and second legs that are interconnected by a hinge portion. The least one retainer is supported on the housing and has tabs that extend in a direction transverse to the transverse axis defined by the dividing walls. The tabs are positioned to engage the first and second legs of the clips to urge the first leg onto the first support surface of a respective support member and to urge the second leg onto the second support surface of a respective support member.

Another aspect of the disclosure is directed to a clip cartridge including a housing and a retainer. The housing includes a body having side walls defining a central cavity and a plurality of dividing walls extending across the central cavity. Each of the plurality of dividing walls defines a transverse axis and forms a clip recess within the central cavity with an adjacent one of the plurality of dividing walls. A support member is positioned within each of the clip recesses and includes a first support surface and a second support surface. A clip is supported within each of the clip recesses of the housing. Each of the clips has a first leg, a second leg, and a hinge portion interconnecting the first and second legs. The retainer is supported on the housing and has tabs that extend in a direction transverse to the transverse axis defined by the dividing walls. The tabs are positioned to engage the first and second legs of the clips to urge the first leg onto the first support surface of a respective support member and to urge the second leg onto the second support surface of a respective support member.

Another aspect of the disclosure is directed to a clip cartridge including a housing and a plurality of retainers. The housing includes a body having side walls defining a central cavity and a plurality of dividing walls extending across the central cavity. Each of the plurality of dividing walls defines a transverse axis and forms a clip recess within the central cavity with an adjacent dividing wall. A support member is positioned within each of the clip recesses and includes a first support surface and a second support surface. A clip is supported within each of the clip recesses on the support member. Each of the clips has a first leg, a second leg, and a hinge portion interconnecting the first and the second legs. The plurality of retainers is supported on the housing. Each of the plurality of retainers is supported on one of the plurality of dividing walls and includes tabs that extend in a direction transverse to the transverse axes defined by the plurality of dividing walls. The tabs are positioned to engage the first and second legs of the clips in the clip recesses located adjacent to the dividing wall to urge the first legs of the respective clips onto the first support surfaces of the respective support members and to urge the second legs of the respective clips onto the second support surfaces of the respective support members.

In aspects of the disclosure, each of the first and second support surfaces of the support member is linear.

In some aspects of the disclosure, each of the support members includes spacers that are positioned between the dividing walls and define slots that are configured to receive a clip of the plurality of clips, wherein the first and second support surfaces are positioned within the slot.

In certain aspects of the disclosure, the retainer includes side walls and a top wall that define a cavity that is configured to receive an upper end of the housing.

In aspects of the disclosure, the top wall of the retainer includes openings and the housing includes a top surface having protrusions, wherein the protrusions are received within the openings to secure the retainer to the housing.

In some aspects of the disclosure, the retainer includes a body that defines an opening that is aligned with the central cavity of the housing and the body includes a plurality of resilient strips that extend across the opening, wherein each of the resilient strips supports the tabs and is aligned with a respective one of the plurality of dividing walls.

In certain aspects of the disclosure, the bodies of the housing and of the retainer are rectangular.

In aspects of the disclosure, each of the retainers includes an H-shaped body having a central portion, and the tabs are supported on each end of the central portion.

In some aspects of the disclosure, the central portion of each of the retainers is supported on a respective one of the plurality of dividing walls such that the tabs of each of the retainers extend above the clip recesses adjacent to the respective dividing wall.

In certain aspects of the disclosure, the central portion of each of the at least one retainer defines an opening and each of the at least one dividing wall includes a protrusion, wherein the opening receives the protrusion to secure the at least one retainer to the respective dividing wall of the housing.

In aspects of the disclosure, the at least one retainer is formed of a translucent material.

In aspects of the disclosure, the retainer includes a body that defines an opening that is aligned with the central cavity of the housing and the body includes a plurality of resilient strips that extend across the opening, wherein each of the resilient strips supports the tabs and is aligned with a respective one of the plurality of dividing walls.

Other features of the disclosure will be appreciated from the following description.

BRIEF DESCRIPTION OF THE DRAWINGS

Various aspects of the disclosed ligation clip cartridge are described herein below with reference to the drawings, wherein.

DETAILED DESCRIPTION

The disclosed ligation clip cartridge will now be described in detail with reference to the drawings in which like reference numerals designate identical or corresponding elements in each of the several views. However, it is to be understood that the disclosed aspects are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, distal, proximal, and similar terms are used to assist in understanding the description and are not intended to limit the disclosure.

In this description, the term "clinician" is used generally to refer to medical personnel including doctors, nurses, and support personnel.

Figure 1:
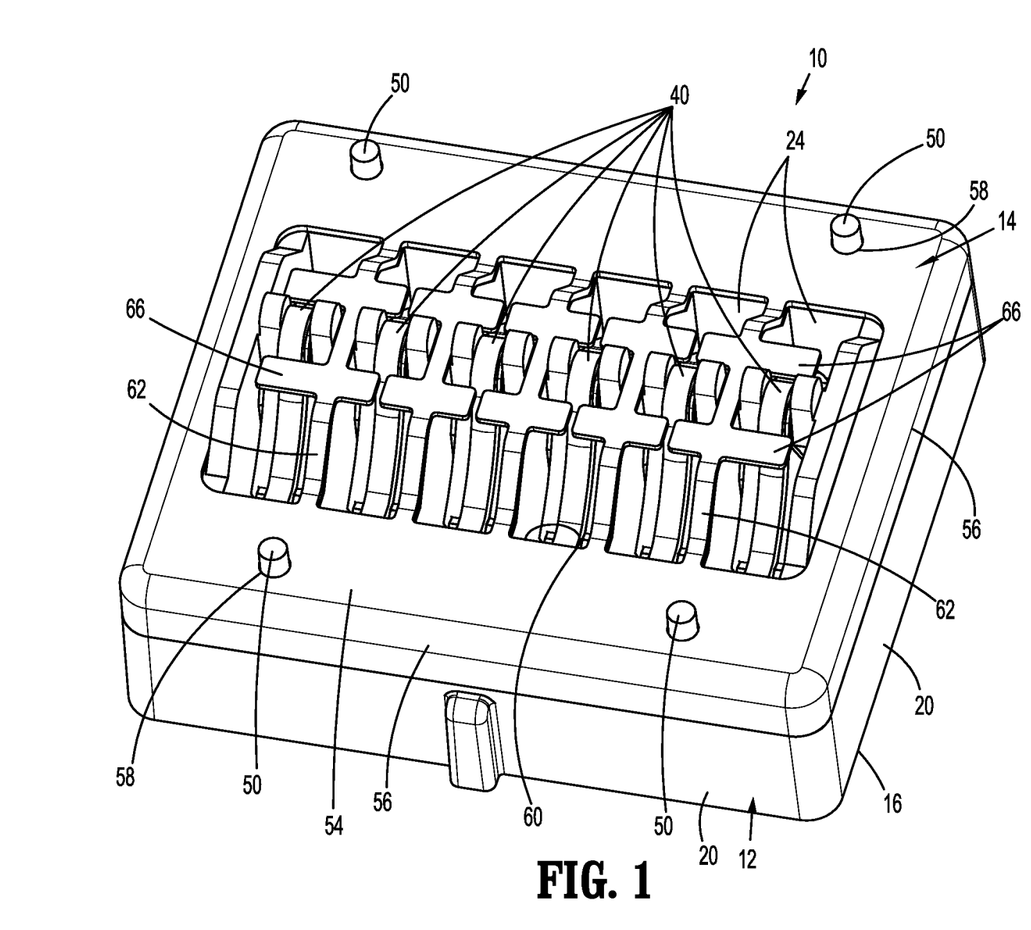
FIG. 1 is a perspective first side view from above of an exemplary embodiment of the disclosed ligation clip cartridge.
Figure 1A:
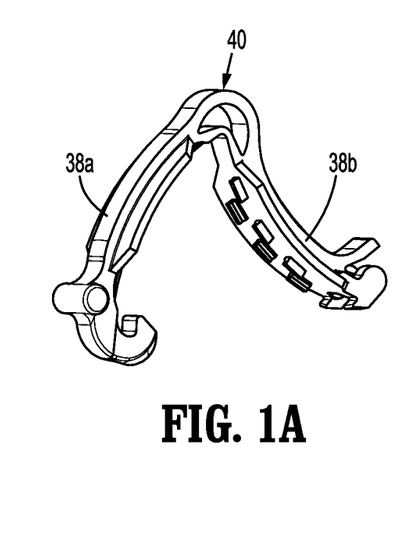
FIG. 1A is a side perspective view of an exemplary embodiment of a ligation clip of the ligation clip cartridge shown in FIG. 1.
Figure 2:
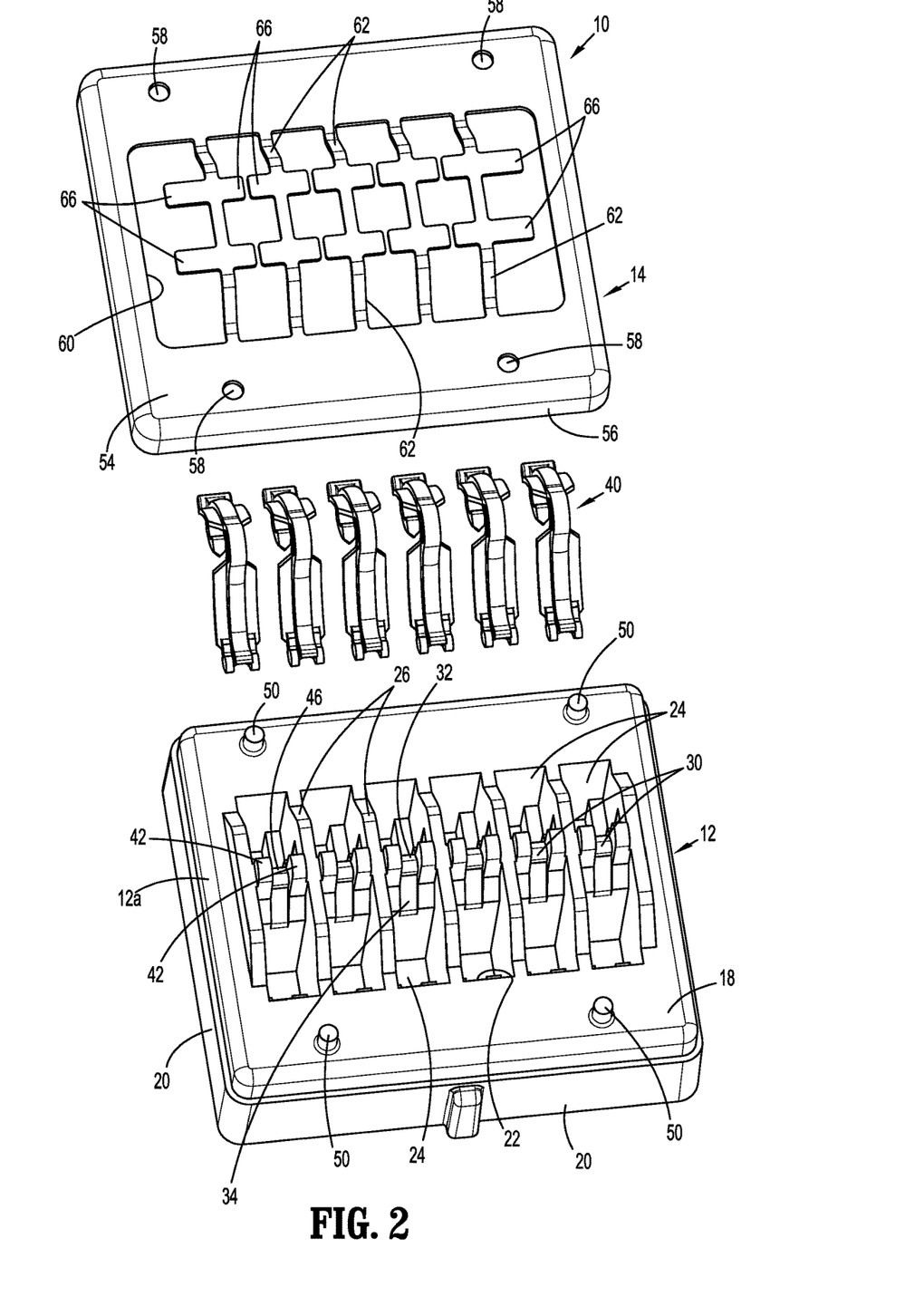
FIG. 2 is an exploded perspective view of the ligation clip cartridge shown in FIG. 4.
Figure 3:
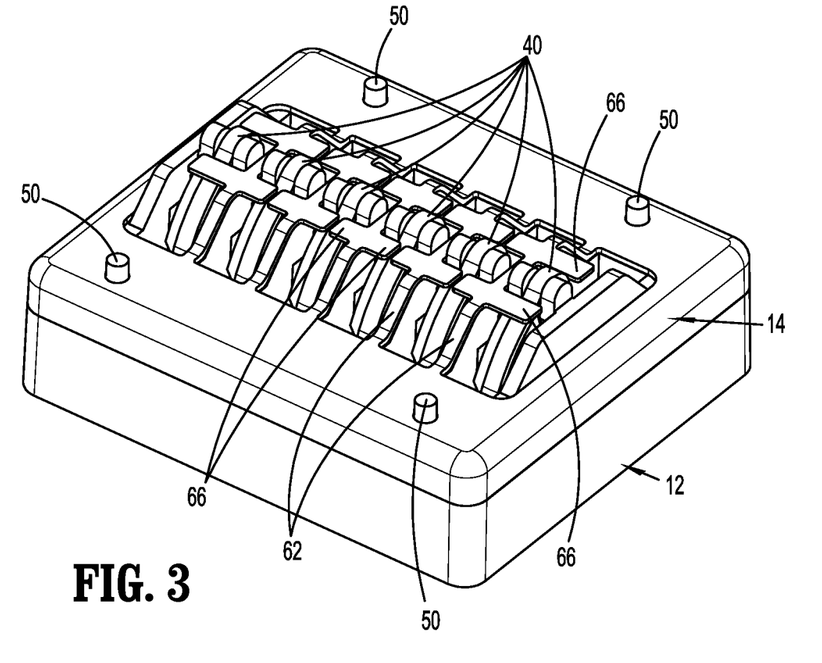
FIG. 3 is a perspective second side view from above of the disclosed ligation clip cartridge shown in FIG. 1.
Figure 4:
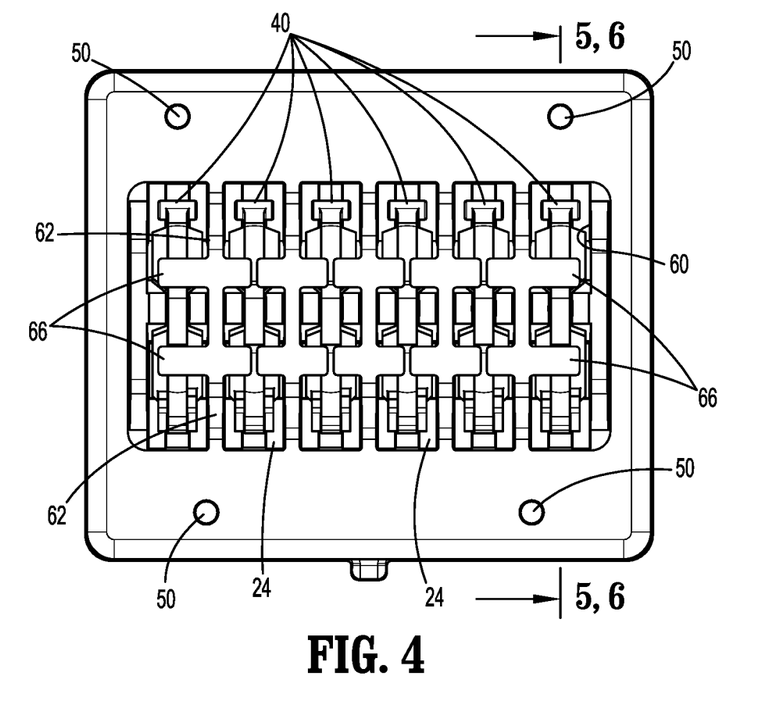
FIG. 4 is a top view of the clip cartridge shown in FIG. 3.
Figure 5:
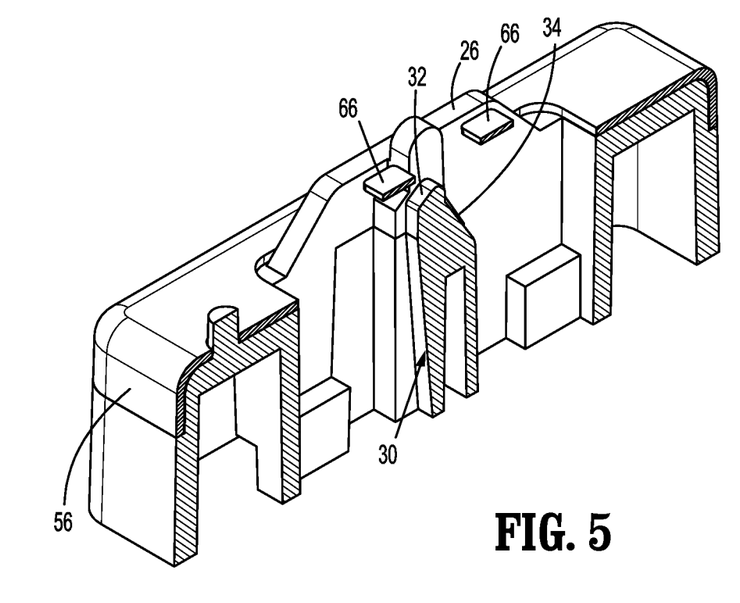
FIG. 5 is a cross-sectional view taken along section line 5-5 of FIG. 4.
Figure 6:
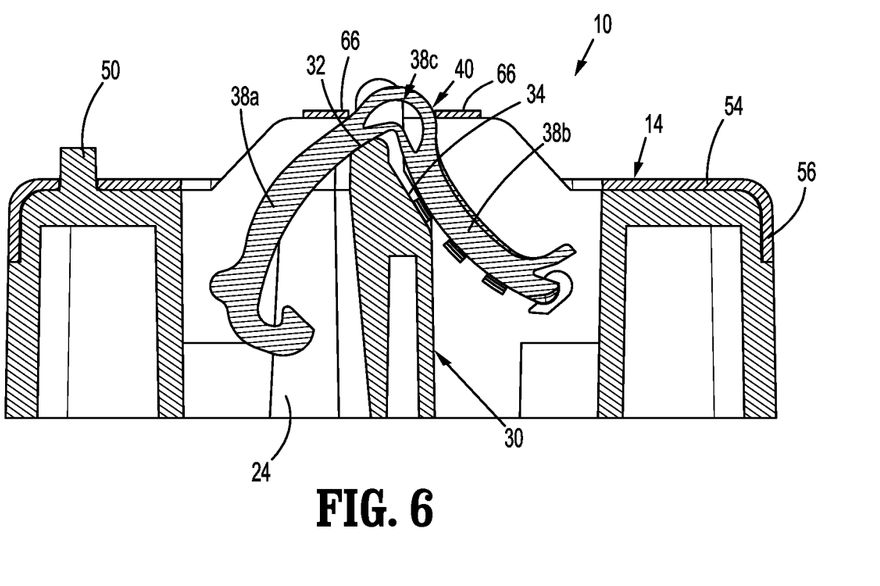
FIG. 6 is a cross-sectional view taken along section line 6-6 of FIG. 4.

FIGS. 1-6 illustrate an exemplary embodiment of the disclosed clip cartridge shown generally as clip cartridge 10. The clip cartridge 10 includes a housing 12 and a retainer 14 that is supported on the housing 12. The housing 12 includes a rectangular body 16 having a top surface 18 (FIG. 2), side walls 20, and a central cavity 22 (FIG. 2) defined by the side walls 20. The central cavity 22 is divided into a plurality of clip recesses 24 by dividing walls 26 that extend upwardly of the top surface 18 of the housing 12 and define transverse axes. Each of the clip recesses 24 includes a support member 30 (FIG. 6) that is positioned between adjacent dividing walls 26 and has a first planar and linear clip support surface 32 (FIG. 5) and a second planar and linear clip support surface 34. The first and second support surfaces 32, 34, respectively, are configured to support legs 38a, 38b of a clip 40 that is supported within the respective clip recess 24. The legs 38a, 38b are coupled together at a hinge portion 38c of the clip 40. The housing 12 also includes spacers 42 (FIG. 2) positioned on each side of the support member 30 that define a slot 46 within the clip recess 24 in which the support member 30 is positioned.

The housing 12 can be molded from a plastic material such as a thermoplastic material although the use of other materials including metals to form the housing 12 is envisioned. In aspects of the disclosure, the top surface 18 of the housing 12 includes a plurality of protrusions 50 that extend upwardly from the top surface 18. The protrusions 50 are provided to couple the housing 12 to the retainer 14 as described in further detail below.

The retainer 14 (FIG. 2) is rectangular in shape and includes a top wall 54 and sidewalls 56 that define a cavity configured to receive an upper end 12a (FIG. 2) of the housing 12. The top wall 54 of the retainer 14 includes openings 58 that receive the protrusions 50 to secure the retainer 14 to the top surface 18 (FIG. 2) of the housing 12. Alternately, other securement techniques can be used to secure the retainer 14 to the housing 12 of the clip cartridge 10.

The top wall 54 of the retainer 14 defines a rectangular opening 60 that is aligned with the central cavity 22 of the housing 12 to provide access to the central cavity 22 and includes a plurality of resilient strips 62 that extend across the opening 60. Each of the resilient strips 62 is aligned with one of the dividing walls 26 of the housing 12 when the retainer 14 is secured to the housing 12 and includes spaced tabs 66. The spaced tabs 66 extend in a direction transverse to the dividing wall 26 to opposite sides of the dividing wall 26 to positions atop the legs 38a, 38b of the clips 40 received in the slots 46.

In aspects of the disclosure, the resilient strips 62 extend upwardly from the top wall 54 of the retainer 12 along the respective dividing walls 26 to position the tabs 66 in engagement with the legs 38a, 38b of each of the clips 40 at a location adjacent the hinge portion 38c of the clip 40. When the retainer 14 is attached to the housing 12, the tabs 66 of the retainer 14 press downwardly on the legs 38a, 38b of the clips 40 to urge the clip 40 onto the support surfaces 32, 34 of the support member 30 to retain the clips 40 within the clip cartridge 10 in an unbiased, unclamped state.

During loading of a clip 40 between the jaws of a clip applier (not shown), the jaws of the clip applier are inserted into a clip recess 24 to access a clip 40. The tabs 66 of the retainer 14 are formed of a resilient material and will deform outwardly upon removal of a clip 40 from a recess 24 of the housing 12. In aspects of the disclosure, the retainer 14 is formed of a translucent material to allow a clinician to more easily visualize a clip 40 within the housing 12 of the clip cartridge 10 during loading.

Figure 7:
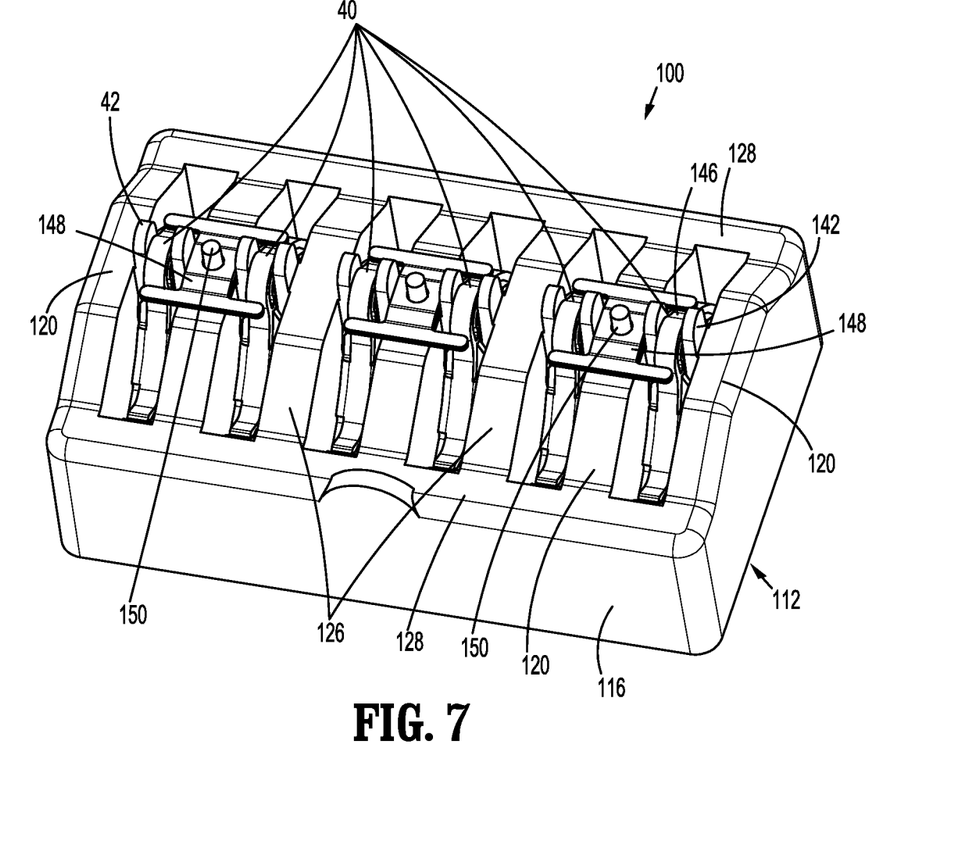
FIG. 7 is a perspective first side view from above of another exemplary embodiment of the disclosed ligation clip cartridge.
Figure 8:
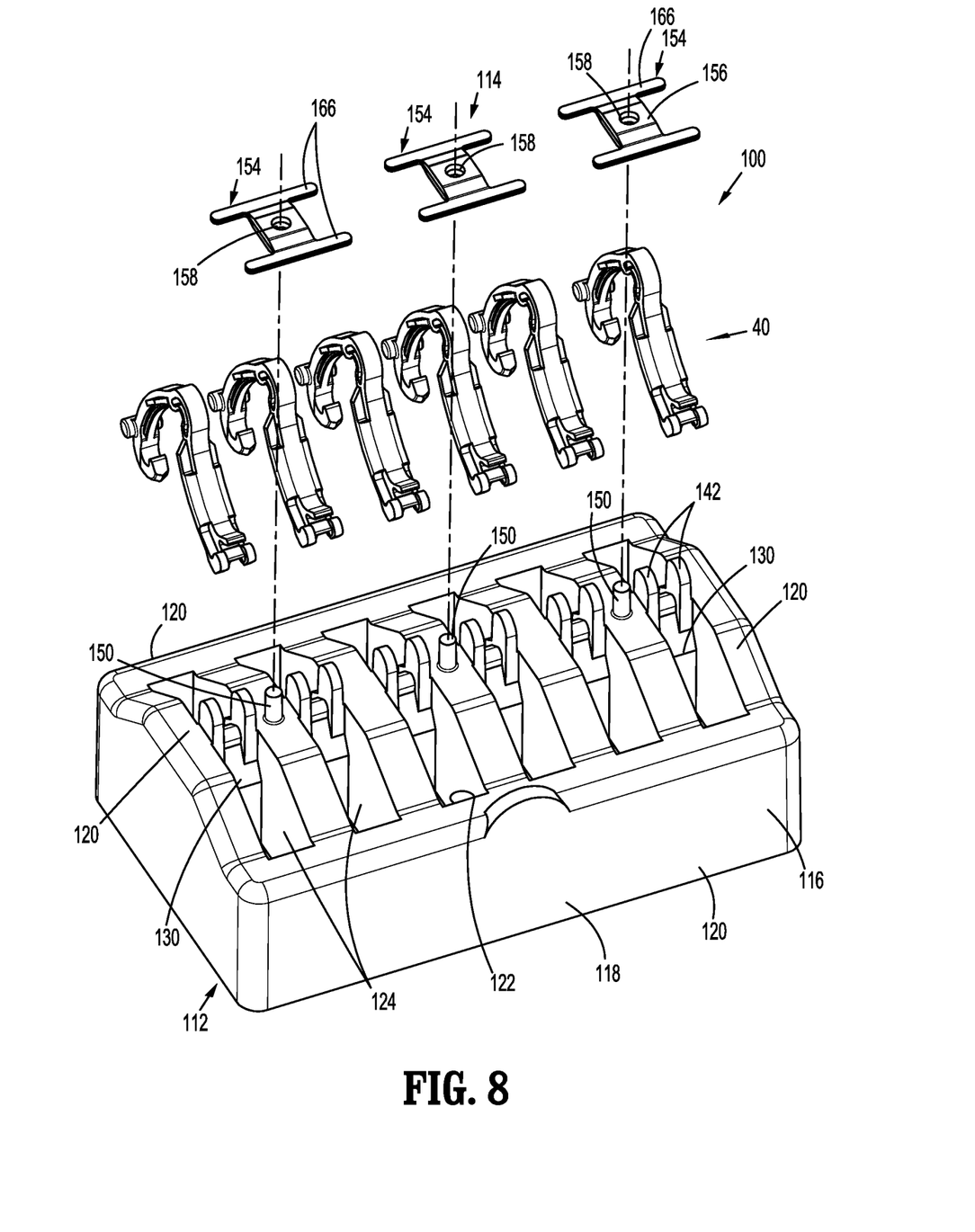
FIG. 8 is an exploded perspective view of the ligation clip cartridge shown in FIG. 9.
Figure 9:
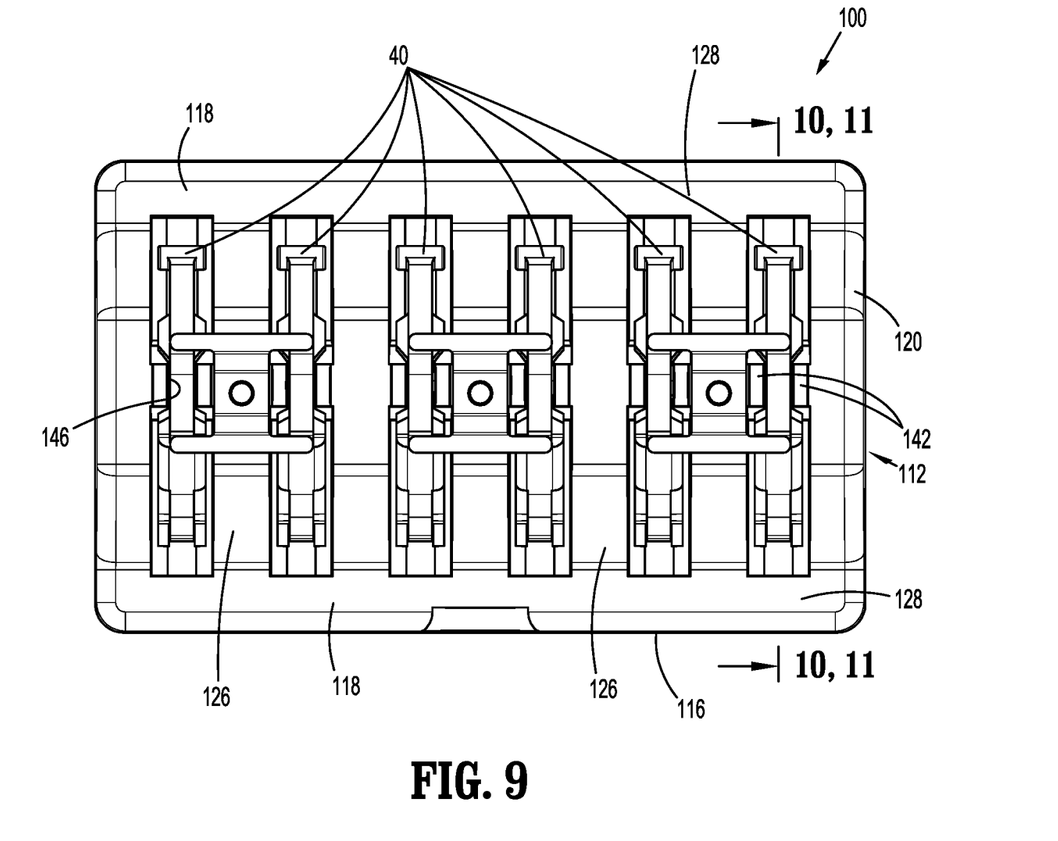
FIG. 9 is a top view of the ligation clip cartridge shown in FIG. 8.
Figure 10:
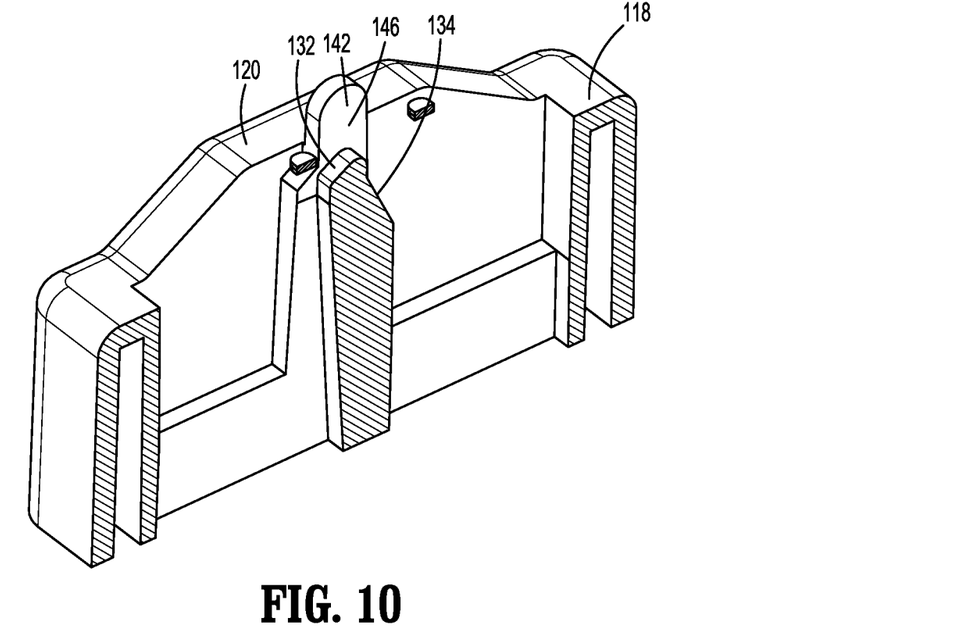
FIG. 10 is a cross-sectional view taken along section line 10-10 of FIG. 9.
Figure 11:
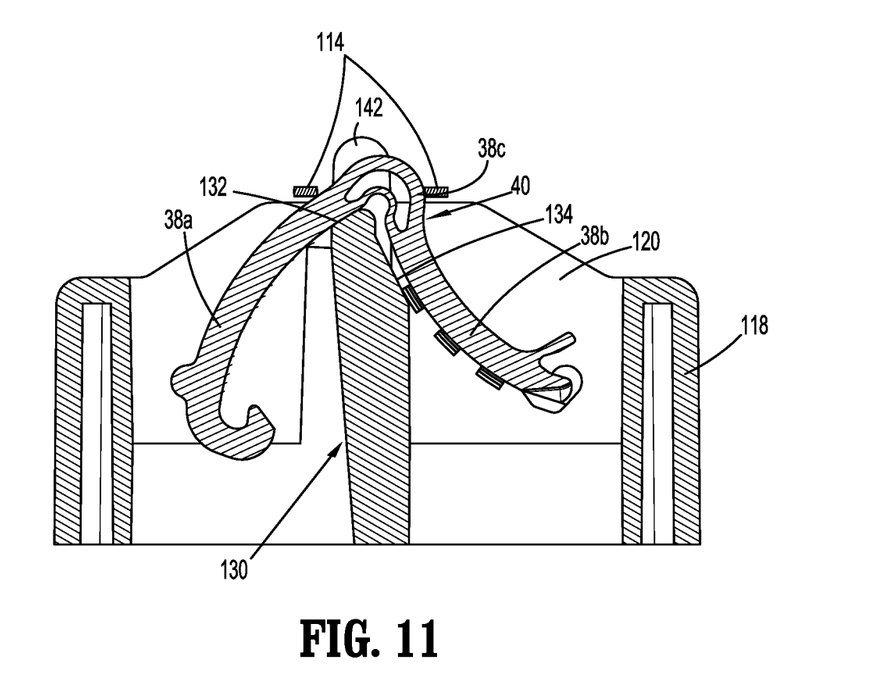
FIG. 11 is a cross-sectional view taken along section line 11-11 FIG. 9.

FIGS. 7-11 illustrate another exemplary embodiment of the disclosed clip cartridge which is shown generally as clip cartridge 100. The clip cartridge 100 includes a housing 112 and a plurality of retainers 114 that are supported on the housing 112. The housing 112 includes a rectangular body 116 having longitudinal side walls 118 and transverse side walls 120 that define a central cavity 122. The central cavity 122 is divided into a plurality of clip recesses 124 by dividing walls 126, each of which define a transverse axis. The transverse side walls 120 and the dividing walls 126 extend upwardly of a top surface 128 of the longitudinal side walls 118 of the housing 112. Each of the clip recesses 124 includes a support member 130 that is positioned between adjacent dividing walls 126 and has a first linear clip support surface 132 (FIG. 10) and a second linear clip support surface 134. The first and second support surfaces 132, 134, respectively, are configured to support legs 38a, 38b of clips 40 supported within the respective clip recesses 124 as described above in regard to support surfaces 32, 34 (FIG. 6). As described above, the legs 38a, 38b of the clips 40 are coupled together at a hinge portion 38c of the clips 40. The support member 130 also includes spacers 142 positioned on each side of the support member 130 between the dividing walls 126 that define slots 146 within which the support members 130 are positioned.

Each of the dividing walls 126 includes a central portion 148 located between the longitudinal side walls 118 of the housing 112. The central portion 148 supports a protrusion 150 that extends upwardly from the dividing wall 126. The protrusions 150 are provided to couple the retainers 114 to the housing 112.

Each of the retainers 114 has a resilient H-shaped body 154 (FIG. 8) including a central body portion 156 and tabs 166 supported at each end of the central body portion 156. The central body portion 156 of each of the retainers 114 defines a bore 158 that receives one of the protrusions 150 extending from the central portion 148 of a respective dividing wall 126 to secure the retainer 114 to the dividing wall 126. When the retainers 114 are attached to the dividing walls 126 of the housing 112 of the clip cartridge 100, the tabs 166 of the retainers 114 press downwardly on the legs 38a, 38b of the clips 40 in the clip recesses 124 on each side of the respective dividing wall 126 to urge the clip 40 onto the support surfaces 132, 134 of the support member 130 to retain the clips 40 within the clip cartridge 100 in an unbiased state.

During loading of a clip 40 between the jaws of a clip applier (not shown), the jaws of the clip applier are inserted into a clip recess 124 to access a clip 40. The tabs 166 of the retainer 114 associated with the clip recess 124 are formed of a resilient material and will deform outwardly upon removal of the clip 40 from the recess 24 of the housing 112. In aspects of the disclosure, the retainer 114 is formed of a translucent material to allow a clinician to more easily visualize a clip 40 within the housing 112 of the clip cartridge 100 during loading.

The disclosed exemplary aspects of the disclosure of the ligation clip cartridge retain clips within the cartridge in an unbiased state to minimize damage to the clip material caused by strain on the clip. As such, the clip can be stored for longer periods of time.

Persons skilled in the art will understand that the devices and methods specifically described herein and illustrated in the accompanying drawings are non-limiting exemplary aspects of the disclosure. It is envisioned that the elements and features illustrated or described in connection with one exemplary embodiment may be combined with the elements and features of another without departing from the scope of the disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. A clip cartridge comprising; a housing including a body having side walls defining a central cavity and a plurality of dividing walls extending across the central cavity, each of the plurality of dividing walls defining a transverse axis and forming a clip recess within the central cavity with an adjacent one of the plurality of dividing walls, and a support member positioned within each of the clip recesses, the support member including a first support surface and a second support surface; a plurality of clips supported within the central cavity of the housing, one of the plurality of clips being supported within each of the clip recesses on the support member, each of the plurality of clips having a first and a second leg that are interconnected by a hinge portion; and at least one retainer supported on the housing, the at least one retainer having tabs that extend from a position adjacent one of the plurality of dividing walls towards the adjacent one of the dividing walls at least partly across the clip recess in a direction transverse to the transverse axis defined by the dividing walls, the tabs being positioned to engage the first and second legs of the plurality of clips to urge the first leg onto the first support surface of a respective support member and to urge the second leg onto the second support surface of a respective support member, wherein the tabs define an H-shape with a member extending therebetween.

2. The clip cartridge of claim 1, wherein each of the first and second support surfaces of the support member is linear.

3. The clip cartridge of claim 1, wherein each of the support members includes spacers positioned between the dividing walls, the spacers defining a slot configured to receive a clip of the plurality of clips, the first and second support surfaces positioned within the slot.

4. The clip cartridge of claim 1, wherein the at least one retainer includes side walls and a top wall, the side walls and the top wall defining a cavity configured to receive an upper end of the housing.

5. The clip cartridge of claim 4, wherein the top wall of the at least one retainer includes openings and the housing includes a top surface having protrusions, the protrusions received within the openings to secure the at least one retainer to the housing.

6. The clip cartridge of claim 1, wherein the at least one retainer includes a body that defines an opening that is aligned with the central cavity of the housing, the body including a plurality of resilient strips that extend across the opening, each of the resilient strips supporting the tabs and being aligned with a respective one of the plurality of dividing walls.

7. The clip cartridge of claim 1, wherein the at least one retainer comprises a body and the bodies of the housing and of the at least one retainer are rectangular.

8. The clip cartridge of claim 1, wherein the at least one retainer comprises a plurality of retainers, each of the at least one retainer includes tabs defining an H-shape with a member extending therebetween.

9. The clip cartridge of claim 8, wherein each member extending between the tabs is supported on a respective one of the plurality of dividing walls such that the tabs of each of the at least one retainer extend above the clip recesses adjacent to the respective dividing wall.

10. The clip cartridge of claim 9, wherein each member extending between the tabs defines an opening and each of the dividing walls includes a protrusion, the opening receiving one of the protrusions to secure the at least one retainer to the respective dividing wall of the housing.

11. The clip cartridge of claim 1, wherein the at least one retainer is formed of a translucent material.

12. A clip cartridge comprising; a housing including a body having side walls defining a central cavity and a plurality of dividing walls extending across the central cavity, each of the plurality of dividing walls defining a transverse axis and forming a clip recess within the central cavity with an adjacent one of the plurality of dividing walls, and a support member positioned within each of the clip recesses, the support member including a first support surface and a second support surface; a clip supported within each of the clip recesses of the housing on the support member, each of the clips having a first leg, a second leg, and a hinge portion interconnecting the first and second legs; and a retainer supported on the housing, the retainer having tabs that extend from a position adjacent one of the plurality of dividing walls towards the adjacent one of the dividing walls across the clip recess in a direction transverse to the transverse axis defined by the dividing walls, the tabs being positioned to engage the first and second legs of the clips to urge the first leg onto the first support surface and to urge the second leg onto the second support surface of a respective support member, wherein the tabs define an H-shape with a member extending therebetween.

13. The clip cartridge of claim 12, wherein the retainer includes a body that defines an opening that is aligned with the central cavity of the housing, the body including a plurality of resilient strips that extend across the opening, each of the resilient strips supporting the tabs and being aligned with a respective one of the plurality of dividing walls.

14. The clip cartridge of claim 12, wherein the retainer includes side walls and a top wall, the side walls and the top wall defining a cavity configured to receive an upper end of the housing.

15. The clip cartridge of claim 12, wherein the retainer is formed of a translucent material.

16. The clip cartridge of claim 12, wherein the retainer includes side walls and a top wall that define a cavity that receives an upper end of the housing, the top wall of the retainer defining openings and the housing including a top surface having protrusions, the protrusions received within the openings to secure the retainer to the housing.

* * * * *